(12) United States Patent
Behme et al.

(10) Patent No.: US 9,080,937 B2
(45) Date of Patent: Jul. 14, 2015

(54) APPARATUS AND A METHOD FOR INVESTIGATING A SAMPLE BY MEANS OF SEVERAL INVESTIGATION METHODS

(71) Applicant: JPK INSTRUMENTS AG, Berlin (DE)

(72) Inventors: Gerd Behme, Berlin (DE); Tilo Jankowski, Berlin (DE); Torsten Jähnke, Berlin (DE)

(73) Assignee: JPK INSTRUMENTS AG (DE)

( * ) Notice: Subject to any disclaimer, the term of this patent is extended or adjusted under 35 U.S.C. 154(b) by 52 days.

(21) Appl. No.: 13/937,237

(22) Filed: Jul. 9, 2013

(65) Prior Publication Data

US 2014/0016119 A1    Jan. 16, 2014

(30) Foreign Application Priority Data

Jul. 10, 2012  (DE) .......................... 10 2012 013 855

(51) Int. Cl.
   *G06K 9/74*     (2006.01)
   *G01N 21/00*    (2006.01)
   *G01Q 60/02*    (2010.01)
   *G01N 21/65*    (2006.01)

(52) U.S. Cl.
   CPC ............... *G01N 21/00* (2013.01); *G01N 21/65* (2013.01); *G01Q 60/02* (2013.01)

(58) Field of Classification Search
   CPC ............ G01B 21/1717; G01B 21/55; G01N 21/65–21/658; G01N 2012/651–2021/656
   USPC .......................... 356/72–73; 850/33, 9, 62–63
   See application file for complete search history.

(56) References Cited

U.S. PATENT DOCUMENTS

| | | | | |
|---|---|---|---|---|
| 5,479,024 A * | 12/1995 | Hillner et al. | ............ | 250/458.1 |
| 6,002,471 A * | 12/1999 | Quake | ............ | 356/73 |
| 6,545,276 B1 * | 4/2003 | Sasaki | ............ | 850/30 |
| 6,643,012 B2 * | 11/2003 | Shen et al. | ............ | 356/301 |
| 6,985,223 B2 * | 1/2006 | Drachev et al. | ............ | 356/301 |
| 7,247,842 B1 * | 7/2007 | Quake et al. | ............ | 250/234 |
| 7,528,947 B2 * | 5/2009 | Banin et al. | ............ | 356/301 |
| 7,977,636 B2 * | 7/2011 | Raschke | ............ | 250/338.1 |
| 2007/0035724 A1 * | 2/2007 | Banin et al. | ............ | 356/236 |
| 2008/0278722 A1 * | 11/2008 | Cunningham et al. | ....... | 356/317 |
| 2009/0066934 A1 * | 3/2009 | Gao et al. | ............ | 356/73 |
| 2009/0119808 A1 * | 5/2009 | Giakos | ............ | 850/31 |
| 2011/0113516 A1 * | 5/2011 | Fink et al. | ............ | 850/9 |
| 2012/0320368 A1 * | 12/2012 | Jiao et al. | ............ | 356/72 |
| 2014/0310839 A1 * | 10/2014 | Wickramasinghe | ........... | 850/40 |

* cited by examiner

*Primary Examiner* — Kara E Geisel
*Assistant Examiner* — Dominic J Bologna
(74) *Attorney, Agent, or Firm* — Schmeiser, Olsen & Watts, LLP

(57) ABSTRACT

A sample carrier suitable for receiving a sample, a first investigation device for investigating the sample and having a first optical beam path for a first measurement light, a second investigation device for investigating the sample and having a second optical beam path for a second measurement light, wherein the first or the second investigation device comprises a probe microscope suitable for investigating the sample and an optical component having a light-permeable section for the first measurement light and an at least partially reflecting section for the second measurement light and disposed in the first and in the second beam path such that the first optical beam path is formed by a material of the optical component in the light-permeable section and that the second optical beam path is formed with a light-reflecting deflection at the at least one partially reflecting section is provided. An associated method is also provided.

14 Claims, 3 Drawing Sheets

APPARATUS AND A METHOD FOR INVESTIGATING A SAMPLE BY MEANS OF SEVERAL INVESTIGATION METHODS

FIELD OF TECHNOLOGY

The following relates to an apparatus and a method for investigating a sample by means of several investigation methods.

BACKGROUND

There are numerous methods in which superstructures are required to investigate a non-transparent sample which require and therefore restrict the geometric space in the vicinity of the sample. As an example, mention may be made here of the desire to examine the object optically with high resolution. For this purpose an objective is required which, with a high numerical aperture and good imaging properties, is usually at a short distance from the object and has a diameter of a few centimeters.

A further method, for example, a probe microscope, must now make do with the available space. In this case, however, an optimal superstructure also requires that the probe and its holder and adjuster are arranged very compactly. A deviation from this principle usually results in an embodiment which is no longer optimal in the sense of the measurement. Accordingly, a compromise must be found in which the quality of the optical method and the quality of the other methods must be weighed up against one another. In the case of the probe microscope, in most cases light is used for detection in order, for example, to determine the deflection of the cantilever. It can also be the case that the two methods must be operated in combination. This is the case, for example, for TERS ("Tip-Enhanced Raman Spectroscopy"), a method in which light is guided onto the tip of a probe microscope and returning light is supplied to a Raman analysis.

SUMMARY

One aspect relates to an apparatus and a method for investigating a sample by means of several investigation methods which, in an integrated measurement system, facilitates the non-colliding use of the investigation methods executed with the aid of various investigation devices on one and the same sample. The apparatus may investigate a sample by means of several investigation methods according to the independent claim 1 and a method for investigating a sample by means of several investigation methods according to the independent claim 13. Exemplary embodiments are the subject matter of dependent claims.

An apparatus for investigating a sample by means of several investigation methods is provided comprising a sample carrier which is suitable for receiving a sample to be investigated in a sample receiving region. The sample carrier can consist of one or several materials. It can have sections which are transparent to light and/or not transparent to light. It can be provided that the sample carrier comprises a flat component, for example, a sample carrier plate. The sample carrier can be received at a retaining device. The apparatus has a first and a second investigation device which are suitable for providing a first and a second method of investigation different from the first for a determination of the sample. With the aid of the investigation devices, a sample disposed in the sample receiving region of the sample carrier can be investigated in various ways, in particular to detect different measurement results for the sample. In this case, the sample can be received on the sample carrier in a fluid environment, for example, a liquid environment.

The first investigation device has a first optical beam path for a first measurement light which is used in the first investigation method. Light beams of the first measurement light are guided along the first optical beam path when executing the first investigation method. The second investigation device has a second beam path for a second measurement light along which light beams of the second measurement light run when executing the second investigation method. It can be provided that the first and the second beam path overlap in one or more subsections which can be formed separately or cohesively. With the apparatus, an integrated measurement system is provided which enables the investigation of samples using several different investigation methods.

The first and/or the second investigation device comprise a probe microscope by which means the sample to be investigated can be investigated by probe microscopy. In the respective investigation device, the probe microscope can be functionally assigned the first/second optical beam path in such a manner that the first/second measurement light is used in the probe-microscopic investigation of the sample in order to guide the measurement light along the beam path. Probe microscopes are known in various designs as such, for example, as a scanning probe microscope, for example, in the form of an atomic force microscope.

The apparatus furthermore has an optical component which has a light-permeable section in which the material of the optical component is at least partially transparent at least for the first measurement light. The transparency of the material of the optical component in the light-permeable section can provide an almost complete transmission or only a partial transmission for the first measurement light. The optical component has an at least partially reflecting section, for example, an at least partially reflecting surface, which is designed to be light-reflecting at least for the second measurement light. As a result, light beams of the second measurement light are reflected at the at least partially reflecting surface. The reflection can be specific or selective, for example, with regard to a wavelength-selective reflection and/or the reflection of selected polarization components. The first optical beam path runs through the material of the optical component in the light-permeable section. The second optical beam path, which is assigned to the second investigation device, exhibits a deflection of the light beams at the at least one partially reflecting section which is brought about by light reflection. The optical component thus enables a configuration both of the first and of the second optical beam path which does not hinder the analysis or investigation of the sample, whether this be at least temporarily simultaneously at different times of the sample investigation. Both investigation methods can be implemented using the respective beam path without mutual hindrance, particularly in the case of a sample which is not transparent (impermeable to light) for the first and/or the second measurement light.

Furthermore, a method for investigating a sample by means of several investigation methods is provided which comprises the following process steps: arranging a sample to be investigated in a sample receiving region of a sample carrier; executing a probe microscopic investigation of the sample using a first investigation method by means of a first investigation device comprising a probe microscope using a first measurement light, where a first optical beam path is formed for the first measurement light which is assigned to the probe microscope; and executing a further investigation of the sample using a second investigation method by means of a second investigation device different from the first using a second measurement light where a second optical beam path is formed here for the second measurement light; where when executing the probe-microscopic investigation, the first optical beam path is formed by a material of the optical component in a light-permeable section of an optical component and where when executing the further investigation, the second optical beam path is deflected at an at least partially reflecting section of the optical component by means of light reflection or conversely. A probe microscope can be provided in conjunction with the first or the second investigation device. In the case of providing a respective probe microscope in the two investigation devices, the first and the second investigation method can comprise a probe-microscopic investigation of the sample.

It can be provided that the sample carrier is received at a retaining device in such a manner that a relative displacement between sample carrier with sample in the sample receiving region on the one hand and elements of the first and/or the second investigation device on the other hand is possible. For example, a relative displacement between a measurement probe or a measurement head of one or both investigation devices relative to the sample can be made possible in this way.

In one embodiment the second beam path can additionally run through the sample carrier, whether this be through an opening formed therein and/or an at least partially transparent material section of the sample carrier for the second measurement light. In general, the optical beam paths are implemented with the aid of light-guiding components, in particular light-conducting and/or light-reflecting components. Light beams of the respective measurement light can then propagate along an optical beam path thus formed in a guided and directed manner. The optical beam path can run in air and/or through any at least partially transparent materials.

The optical component can, for example, comprise a glass or a plastic body. The light-permeable section can be formed in a region of the optical component having mutually plane-parallel end faces. Quite generally the optical component for the optical beam paths assigned to the different investigation methods jointly takes over functional tasks, for example, therefore light deflection and/or light transmission. The optical component is in this respect assigned to both investigation devices.

A further development provides that the optical component has a flat at least partially reflecting surface in the region of the at least partially reflecting surface. The flat at least partially reflecting surface can be formed as an outer surface on the optical component. In one embodiment the flat surface can be disposed substantially parallel to the plane of the sample receipt, for example, in a horizontal position. It can be provided that the parallel arrangement is also retained in an investigation-dependent displacement of the optical component relative to the sample. Here the displacement can be executed free from any change in the reflection behaviour in the region of the at least partially reflecting section.

In one embodiment it can be provided that the optical component is disposed on the first investigation device. In this case, the optical element can be held and mounted on an element of the first investigation device, for example, on the probe microscope. For example, the optical component on the first investigation device can be disposed on a side facing the sample receiving region. If the first investigation device, whether this be in the design with or without the probe microscope, is disposed substantially above the sample carrier, the optical component can be disposed on a lower side of an element of the first investigation device, detachably or non-detachably. In this or other embodiments it can be provided that the optical component is coupled to an adjusting or displacement device which enables the relative position of the optical component to be varied in relation to other components of the apparatus for investigating the sample. For example, the optical component can be received on an adjusting element which enables a displacement in the x, y and/or z direction.

One embodiment provides that the optical component is connected to a displacement device which is assigned to the first and/or the second investigation device in such a manner that as a result of an investigation-dependent displacement executed with the aid of the displacement device in the first and/or the second investigation device, the optical component is co-displaced. A co-displacement of the optical component can take place, for example, if in one of the investigation methods a measurement probe or a measurement head is displaced relative to the sample receiving region with the sample to be investigated. In one embodiment it can be ensured in this way that the relative position of optical component to measurement probe or measurement head is maintained so that in this respect and in this region the associated optical beam path remains unchanged. Here it can also be provided that the optical component can be re-adjusted with the aid of the adjusting device associated with said component.

A further development provides that the sample to be investigated is not transparent at least for the second measurement light. Alternatively the sample to be investigated can be not transparent for the first measurement light or the first and the second measurement light. The transparency or non-transparency of the sample to be investigated can relate to narrower or broader wavelength ranges, for example, the entire visible range of the light or sections thereof. However, a transparent or substantially non-transparent design of the sample can also be given only with respect to individual wavelengths.

In one embodiment it can be provided that the sample carrier consists of a material which is transparent for the second measurement light, at least in sections. In this way it is possible that the second optical beam path is also formed through the sample carrier. Alternatively or additionally to the transparent design of the material of the sample carrier, one or more openings can be provided in the sample carrier to provide a light passage at least for the second measurement light. The sample carrier can be received in a holder which for its part is impermeable to light. The sample carrier holder can be formed along the circumferential edge of the sample carrier on one or more sides, where continuous and/or interrupted retaining sections can be provided.

A further development provides that measurement light beams of the second measurement light on the path towards the sample and/or on the path away from the sample are deflected along the second optical beam path at the at least one partially reflecting section. The measurement light beams of the second measurement light which are guided along the second optical beam path can run through the light-permeable section of the optical component on their path towards the sample receiving region and/or on their path away from the sample receiving region. In this case, the second optical beam path does not necessarily detect a direct interaction of the measurement light beams of the first light with the sample. On the contrary, for example, the second optical beam path can exhibit a light deflection at a measurement probe or a measurement head. Such an investigation method can, for example, be used in probe microscopes, in particular scanning probe microscopes. There a so-called cantilever has a light-reflecting surface at which measurement light beams are deflected. The interaction of the cantilever with the sample to be investigated changes the light deflection of the measurement light and delivers a measurement signal without the measurement light interacting directly with the sample to be investigated. In other investigation methods, for example, fluorescence spectroscopy, exciting light is applied to the sample to be investigated along the optical beam path used. From the sample fluorescence light beams then pass along the optical beam path of the investigation device. The aforesaid explanations apply generally for the various investigation devices of the apparatus described here. The section of the optical beam path away from the sample usually leads to a detector device by which means measurement light beams are detected, whether this be, for example, fluorescence light or measurement light deflected at the cantilever.

In one embodiment it can be provided that measurement light beams of the first measurement light on the path towards the sample and/or on the path away from the sample run along the first optical beam path through the light-permeable section of the optical component. The explanations put forward previously in connection with the measurement light beams of the second measurement light apply accordingly to the measurement light beams of the first measurement light.

In one embodiment it can be provided that the at least partially reflecting section is formed on an inner surface of the optical component. For example, the inner surface can be formed on a prism component. The inner surface can be flat or also curved.

One embodiment provides that the first investigation device is disposed on a side of the sample carrier on which the sample receiving region is formed. The first investigation device can in this case be disposed above the sample carrier. The sample carrier divides the spatial region around the sample receiving region with the sample so that a spatial region above the sample carrier and a spatial region below the sample carrier are provided. The use of the proposed optical component enables the investigation devices, in particular measurement heads or probes provided here, to be displaced in the immediate vicinity above and/or below the sample carrier and consequently at a desired measurement distance from the sample.

A further development preferably provides that the second investigation device is disposed on an opposite side of the sample carrier, facing away from the sample receiving region. If the first investigation device is disposed on one side of the sample carrier, an investigation or measurement system is provided with the embodiment proposed here in which the first investigation device is disposed on one side of the sample carrier and the second investigation device is disposed on the opposite side of the sample carrier. In these or other embodiments it can be provided that the optical component is disposed on one side of the sample carrier, i.e. in particular above the sample carrier.

In one embodiment it can be provided that the first and/or the second investigation device are an investigation device from the following group of investigation devices: atomic force microscope, Raman spectroscope, epi illumination, optical microscope, absorption measurement device and fluorescence measurement device. In the various investigation devices, the respectively associated optical beam path can comprise a light path between a light source, the region around the sample receiving, whether this be in direct or non-direct contact with the sample, and a detector device. In one embodiment, a probe microscope, in particular scanning probe microscope which has a measurement device with a cantilever is disposed above the sample carrier. A Raman spectroscope or spectrometer can be disposed on the underside.

In connection with the method for investigating the sample by means of several investigation methods, the explanations put forward previously for embodiments apply accordingly. It can be provided that the first and the second investigation by means of the first and the second investigation method are conducted at least temporarily simultaneously in such a manner that measurement light beams of the first measurement light pass along the first optical beam path and measurement light beams of the second measurement light pass along the second optical beam path simultaneously. For this embodiment the optical component also supports a collision-free investigation.

At least measurement light beams of the second measurement light can be guided along the second optical beam path on one or more sides of the sample past the sample carrier.

In one embodiment the measurement light beams of one investigation method can be guided past the sample from below and directed from a coated glass surface on the optical component back to the sample. The glass surface itself can be transparent for the measurement light beams of the other method.

The glass surface can be exchangeable and adapted to the particular measurement process.

The coated glass surface on the optical component can be provided with an angle or a curvature. It can be provided to add a further glass surface in order to provide only two parallel effective boundary surfaces for the light of the other investigation method. This can be achieved, for example, by cementing two glass bodies where the cemented surface contains the necessary coating.

Light of different wavelength can be used as differentiation of the measurement beams of the two investigation methods. Alternatively a different differentiation such as, for example, the polarisation can also be used.

A Raman spectrometer or a fluorescence device can be used as one method. Alternatively an epi illumination or another standard method can be provided. A combination of these methods can also be provided. Another method could be illumination.

BRIEF DESCRIPTION

Further exemplary embodiments are explained in detail hereinafter with reference to figures of the drawings. In the figures.

DETAILED DESCRIPTION

Figure 1:
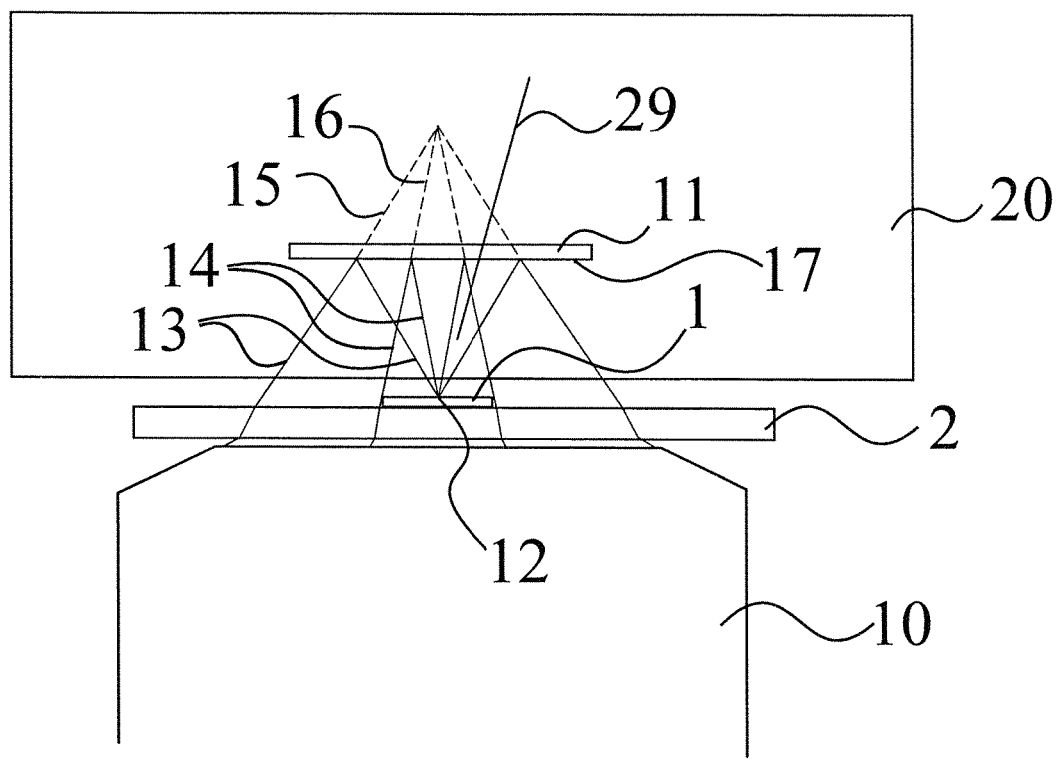
FIG. 1 shows a schematic view of an apparatus for optical investigation of a sample.

FIG. 1 shows a sample 1 which is mounted on a transparent carrier 2. The sample 1 is assumed to be non-transparent. Transparent in this case always relates to the wavelength used in each case, which can also lie in the non-visible range.

By means of the objective 10, light is now sent through the transparent sample carrier 2 and reflected at a glass body 11 having a coating 17 and focussed to the point 12. The coating 17 is reflective at least for the wavelength range of interest.

The light beams are represented by the beams 13 and 14, where 13 represents the outer boundary of the beam and 14 represents the inner boundary since light having a smaller angle of incidence than 13 will not be transmitted by the sample 12. A light cone is thus obtained having a conical cavity in the centre. The smaller the sample 12, the smaller is the cavity. If the glass body 11 did not include the coating 17, light beams 13, 14 would be transmitted through the glass body 11, represented by light beams 15, 16, respectively.

The apparatus 20 for another method which is disposed above the sample 1 is now only restricted by the glass body 11 and the light cone spanned by the beams 13 and 14, which in the ideal case should not be disturbed at all or at least only a little. The other method requires an optical beam path 29 which must pass through the glass body 11. For this purpose the glass body 11 and the coating 17 must be constituted so that both are transparent for the light wavelengths used, at least partially transparent. The beam path 29 can now be used only in one direction or also in both directions. The beam 29 is only shown as an example and it can be the case that the light, for example is emitted or detected over the entire surface 11 in the direction of the sample.

The body 11 can also consist of a different transparent material such as, for example, calcium fluoride. It would also be possible to take a material which has the desired reflecting and transmitting properties without a coating.

The space between 2 and 1 and 11 can also be filled with a fluid without any problems if this is sufficiently transparent for the methods used.

Figure 2:
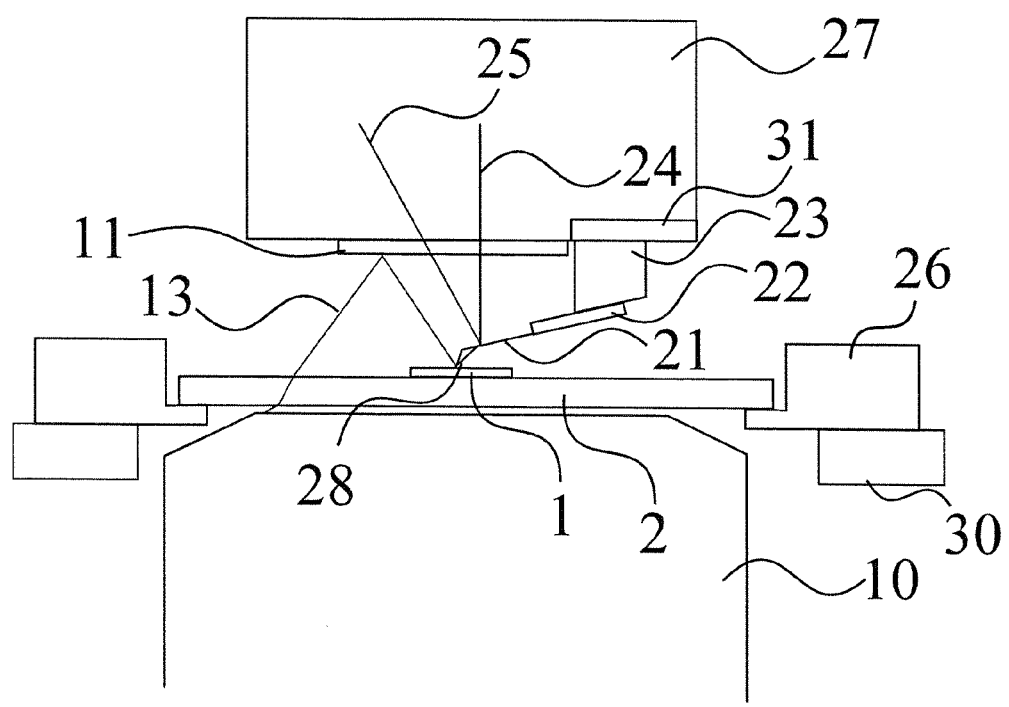
FIG. 2 shows a schematic view of an apparatus for optical investigation of a sample using TERS.

FIG. 2 shows an embodiment of an apparatus for determination of a sample by means of two investigation devices which shows a TERS measurement ("Tip-enhanced Raman Spectroscopy") on a non-transparent sample using a probe microscope which can comprise a scanning probe microscope, in particular an atomic force microscope. Here the two methods work together in the sense that the tip 28 of the cantilever 21 is impinged upon by the light cone reflected at the glass body 11, of which only the left-hand beam 13 is shown here for the sake of clarity. The Raman spectrum amplified by the tip 28 is then measured in reflection, i.e. it is again reflected by the glass body 11 into the objective and then fed behind the objective to a Raman spectrometer not shown. The cantilever 21 is fastened to a chip 22 which for its part is again fastened to a holder 23.

The remaining structure of the probe microscope is designated in summary by the reference number 27. Only the detection light is indicated. The beam 24 is the light focussed onto the cantilever which is frequently produced by a laser and the beam 25 shows the light reflected by the cantilever. Both light beams here pass through the glass body 11 according to the invention. The sample 1 is in turn mounted on a transparent substrate 2 which is again held by the holder 26.

Since it can be very important for TERS that the tip 28 is fixed in relation to the light beam 13, during the TERS measurement the sample is moved over the scanner 30, where a known embodiment would be a piezoscanner in three spatial directions. Other scanners are naturally also feasible. In order that the emitted light 13 effectively illuminates the tip 28, it is generally necessary to carry out a motion. This can either be achieved by means of a movement of the light cone 13 or by means of a movement of the tip 28. The movement of the light cone could be achieved, for example, by executing an angular movement of the light for example in the rear focal plane of the objective. By means of a movement of the objective in the vertical direction the focus could be brought onto the sample. The movement of the tip could be achieved by moving the holder 23 by means of a scanner 31. Here care should be taken to ensure that the detection light remains on the cantilever, for example, by co-scanning it. Naturally the scanner could also be arranged so that the glass body 11 is co-scanned. The space between 1 and 2 and 11 can be filled with a fluid.

Figure 3A:
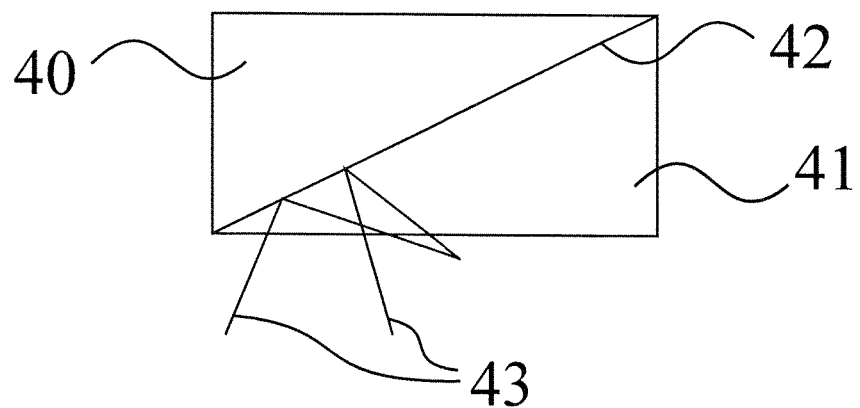
FIG. 3a shows a first schematic view of a glass body which can be used as an optical component.
Figure 3B:
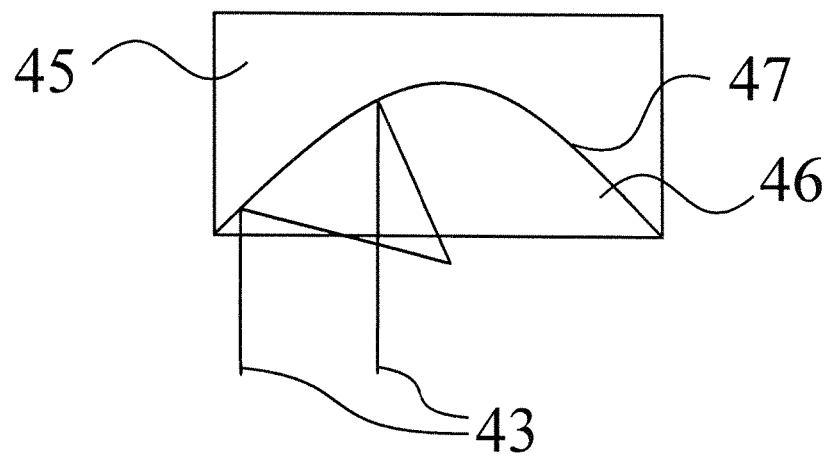
FIG. 3b shows a second schematic view of a glass body which can be used as an optical component.

FIGS. 3a and 3b show other embodiments of the glass body 11 from FIG. 1 and FIG. 2, where glass is only mentioned here as an example of a possible material.

FIG. 3a shows two glass bodies 40 and 41 which are cemented to one another. The sloping boundary surface 42 is coated in the sense of the invention so that it is reflective for wavelengths of one method which is located substantially below the sample and is substantially transparent for wavelengths of the upper method. If, for example, a parallel glass block was used for example for the other method located above the sample, almost nothing changes as a result of the new glass body composed of 40 and 41 and the measurement can take place undisturbed in the usual manner. The possible light beams 43 for example for TERS are indicated. These again come from an objective not shown, which produces a focussing. In this case, the focus lies outside the optic axis of the objective.

FIG. 3b again shows a glass body consisting of two parts 45 and 46 in which the focussing of the light beams 48 required, for example, for TERS is performed by the boundary surface 47 coated in the sense of the invention. An objective for one method could then be dispensed with. In the case of parallel beams 48, the boundary surface 47 would then be hyperbolic-shaped in the optimal case. A spherical surface would certainly be easier to produce but would result in imaging errors. In principle the entire space can be used here. In particular in the case of an atomic force microscope as another method, the cantilever can result in a shadowing.

Other configurations for the boundary surface are naturally also feasible. It would also be possible for the glass body to consist of more than two sub-bodies or of different glasses or materials.

For the embodiments shown in FIGS. 3a and 3b it can be provided to arrange the body movably relative to the tip 28 from FIG. 2 since for TERS for example, the tip must be very accurately impinged upon by the focal point and in particular for the body from FIG. 3b there is only one fixed focal point. It may possibly be sufficient to move the tip with the scanner (31 from FIG. 2) but it can also be the case that a rough adjustment must be made previously so that a good adjustment is found in the region of the scanner.

The features of the invention disclosed in the preceding description, the claims and the drawings can be of importance both individually and in any combination for the implementation of the invention in its various embodiments.

The invention claimed is:

1. An apparatus for investigating a sample by means of several investigation methods comprising:
    a sample carrier suitable for receiving a sample to be investigated in a sample receiving region;
    a first investigation device suitable for investigating the sample according to at least one first investigation method, the first investigation device having a first optical beam path for a first measurement light, wherein the first investigation device comprises a probe microscope suitable for investigating the sample by probe microscopy, and wherein the first investigation device is arranged on a side of the sample carrier on which the sample is received;
    a second investigation device suitable for investigating the sample according to at least one second investigation method different from the at least one first investigation method, the second investigation device having a second optical beam path for a second measurement light, wherein the second investigation device is arranged on a side of the sample carrier opposite to the side on which the sample is received; and an optical component having a light-permeable section for the first measurement light as well as an at least partially reflecting section for the second measurement light and which is disposed in the first optical beam path and in the second optical beam path in such a manner that the first optical beam path is formed by a material of the optical component in the light-permeable section, and that the second optical beam path is formed with a light-reflecting deflection at the at least one partially reflecting section, wherein the optical component is arranged on the side of the sample carrier on which the sample is received.

2. The apparatus according to claim 1, wherein the optical component in the region of the at least partially reflecting section has a flat, at least partially reflecting surface.

3. The apparatus according to claim 1, wherein the optical component is disposed on the first investigation device.

4. The apparatus according to claim 1, wherein the optical component is connected to a displacement device which is assigned to the first investigation device and/or the second investigation device in such a manner that as a result of an investigation-dependent displacement executed with the aid of the displacement device the optical component is co-displaced in the first investigation device and/or the second investigation device.

5. The apparatus according to claim 1, wherein the sample to be investigated is not transparent at least for the second measurement light.

6. The apparatus according to claim 1, wherein the sample carrier/, at least in sections, includes a transparent material for the second measurement light.

7. The apparatus according to claim 1, wherein measurement light beams of the second measurement light on the path towards the sample and/or on the path away from the sample along the second optical beam path are deflected at the at least partially reflecting section.

8. The apparatus according to claim 1, wherein measurement light beams of the first measurement light on the path towards the sample and/or on the path away from the sample along the first optical beam path run through the light-permeable section of the optical component.

9. The apparatus according to claim 1, wherein the at least partially reflecting section is formed on an inner surface of the optical component.

10. The apparatus according to claim 1, wherein the first investigation device is formed on the side of the sample carrier on which the sample receiving region is formed.

11. The apparatus according to claim 1, wherein the second investigation device is formed on the opposite side of the sample carrier facing away from the sample receiving region.

12. The apparatus according to claim 1, wherein the first investigation device and/or the second investigation device comprises an investigation device from the following group of investigation devices: atomic force microscope, Raman spectroscope, epi illumination, optical microscope, absorption measuring device and fluorescence measuring device.

13. A method for investigating a sample by means of several investigation methods comprising the following process steps:

disposing a sample to be investigated in a sample receiving region of a sample carrier;

performing a probe microscopic investigation of the sample using a first investigation method by means of a first investigation device which comprises a probe microscope using a first measurement light, wherein a first optical beam path is formed for the first measurement light which is assigned to the probe microscope, the first investigation device being arranged on a side of the sample carrier on which the sample is received; and performing a further investigation of the sample using a second investigation method by means of a second investigation device different from the first investigation method using a second measurement light, wherein a second optical beam path is formed for the second measurement light, wherein the second investigation device is arranged on a side of the sample carrier opposite to the side on which the sample is received;

wherein, when performing the probe-microscopic investigation, the first optical beam path is formed by a material of an optical component in a light-permeable section of the optical component, wherein, when performing the further investigation, the second optical beam path is deflected at an at least partially reflecting section of the optical component by means of light reflection or conversely;

wherein the optical component is arranged on the side of the sample carrier on which the sample is received.

14. The method according to claim 13, wherein the first investigation and the second investigation are carried out at least temporarily simultaneously in such a manner that measurement light beams of the first measurement light run along the first optical beam path and measurement light beams of the second measurement light run along the second optical beam path simultaneously.

* * * * *